(12) United States Patent
Graetzel et al.

(10) Patent No.: US 9,269,912 B2
(45) Date of Patent: Feb. 23, 2016

(54) METAL COMPLEX COMPRISING A LIGAND HAVING A COMBINATION OF DONOR-ACCEPTOR SUBSTITUENTS

(75) Inventors: Michael Graetzel, Saint Sulpice (CH); Etienne David Baranoff, Birmingham (GB); Mohammad Khaja Nazeeruddin, Ecublens (CH)

(73) Assignee: SOLVAY SA, Brussels (BE)

( * ) Notice: Subject to any disclaimer, the term of this patent is extended or adjusted under 35 U.S.C. 154(b) by 154 days.

(21) Appl. No.: 13/988,267

(22) PCT Filed: Nov. 21, 2011

(86) PCT No.: PCT/EP2011/005851
§ 371 (c)(1),
(2), (4) Date: Sep. 17, 2013

(87) PCT Pub. No.: WO2012/069170
PCT Pub. Date: May 31, 2012

(65) Prior Publication Data
US 2014/0005397 A1    Jan. 2, 2014

(30) Foreign Application Priority Data

Nov. 22, 2010    (EP) .................................. 10192027

(51) Int. Cl.
*C07F 15/00*    (2006.01)
*H01L 51/50*    (2006.01)
*H01L 51/00*    (2006.01)

(52) U.S. Cl.
CPC ........ *H01L 51/0085* (2013.01); *C07F 15/0033* (2013.01); *H01L 51/009* (2013.01)

(58) Field of Classification Search
USPC ................................................ 546/2; 313/504
See application file for complete search history.

(56) References Cited

U.S. PATENT DOCUMENTS

7,585,573 B2 *    9/2009    Lee et al. ...................... 428/690

* cited by examiner

*Primary Examiner* — Charanjit Aulakh (57) ABSTRACT

Disclosed is a metal complex having a partial structure represented by the following Formula (I-0) or a tautomer thereof: formula (I-0) Cy is a 5 to 7 membered heterocyclic ring, preferably a 6-membered ring, which may be aromatic, non aromatic or partially aromatic and which coordinates to the metal atom through a carbon atom; A is a nitrogen atom a is an integer equal or superior to 1; D is an electron donor group; and b is an integer equal or superior to 1.

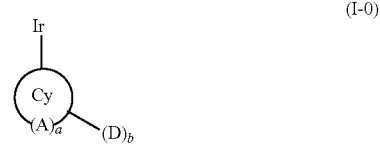

(I-0)

3 Claims, 1 Drawing Sheet

METAL COMPLEX COMPRISING A LIGAND HAVING A COMBINATION OF DONOR-ACCEPTOR SUBSTITUENTS

CROSS REFERENCE TO RELATED APPLICATIONS

The present application is a National Stage of International Application No. PCT/EP2011/005851 filed on Nov. 21, 2011, which claims the benefit of European Patent Application No. 10192027 filed on Nov. 22, 2010, the entire disclosures of which are incorporated herein by reference.

TECHNICAL FIELD

The present invention relates to a complex comprising a ligand with a combination of donor-acceptor substituents and light emitting devices comprising said complex.

BACKGROUND ART

Organic light emitting diodes (OLEDs) contain an organic emissive layer (EML) that emits light by fluorescence or phosphorescence. OLEDs exhibiting highest luminance efficacy and power conversion efficiency are fabricated using electroluminescent materials containing heavy metal atoms. Therefore electroluminescent materials based on transition metal complexes attract widespread attention and enormous amount of research is conducted worldwide in order to improve existing devices. For example, electroluminescent materials comprising complexes with platinum group metals such as platinum (Pt), osmium (Os), ruthenium (Ru) and iridium (Ir) can be used to form an electroluminescent layer in OLEDs, wherein the iridium complexes exhibit the highest efficiency and widest color tuning capability. Iridium complexes exhibiting high luminance efficiency typically have an octahedral structure with the iridium center in a +3 oxidation state. The mechanism of light emission of these iridium complexes is based on a triplet metal to ligand charge transfer ($^3$MLCT) transition between the metal and the ligand, or a triplet ligand-centered ($^3\pi-\pi^*$)transition. Most often the transition responsible for the light emission in transition metal complexes is of mixed LC-MLCT character. The strong spin-orbit coupling induced by the heavy metal center produces high phosphorescence efficiency by efficiently mixing the singlet and triplet states rendering possible and efficient the formally forbidden transition from the triplet-excited state to the singlet-ground state.

One of the best known triplet-state blue phosphorescent complex is the iridium(III) complex Bis(4,6-difluorophenylpyridinato-N,C2)picolinatoiridium (FIrpic), which is already described in various prior references, such as WO 02/15645 and Appl. Phys. Lett. 2001, 79, 2082. However, FIrPic is not sufficiently stable under the operation conditions of typical OLED devices to allow practical commercial applications.

Some references disclose derivatives of FIrpic. In the specification of PCT Publication No. WO05097943 A1, several iridium complexes are disclosed, e.g., complexes I-74 to I-78 on page 32 of the reference. U.S. Pat. No. 7,534,506 and EP Publication No. EP2036907 A1 also relate to metal complexes for organic electroluminescence devices which are substituted by various electron donating and withdrawing groups.

US 2006/0014047 relates to luminescent devices comprising an organic compound layer comprising a metal coordination compound of the formula wherein M may be Ir, Rh or Pd.

EP 2036907 relates to organoluminiscent devices and discloses Pt-complexes of formulae However, none of the above-disclosed materials meets all the requirements necessary for OLED application, particularly thermal/environmental stability which can affect the whole life time of OLED devices, as well as high phosphorescent efficiency. Thus, there has been a need to develop new emissive materials, which are capable of satisfying all of the requirements indicated above.

SUMMARY OF INVENTION

It has been found that the stability of metal complexes can be improved by a new substitution pattern using various donor and acceptor groups when it is used in light emitting devices. Further, fine tuning of HOMO and LUMO energy levels for metal complexes is also possible from the above approach.

In one aspect of the present invention, a metal complex having a partial structure represented by Formula (I-0) or a tautomer thereof is provided:

Formula (I-0)

wherein Cy is a 5 to 7 membered ring, preferably a 6-membered ring, which may be aromatic, non aromatic or partially aromatic and which coordinates to the metal atom through a carbon atom;

A is a nitrogen atom;

a is an integer equal or superior to 1;

D is an electron donor group; and b is an integer equal or superior to 1.

In another aspect of the present invention, a metal complex comprising an organic ligand represented by Formula (I) or a tautomer thereof, is provided as below.

Formula (I)

wherein
A is a nitrogen atom
$D^1$ and $D^2$ are electron donor groups, the same or different at each occurrence, preferably any one selected from a group consisting of amino, $C_1$-$C_{20}$ alkoxy, and $C_1$-$C_{20}$ alkyl groups,
Ca is a neutral ring capable of coordination to the metal atom,
X is independently selected from substituents provided that at least one substituent X is hydrogen
n is an integer from 1 to 2, y is an integer from 1 to 2, with the proviso that n+y is not more than 3,
L is any one selected from a single bond, —S—, —O—, —Se—, >$CR_2$, >NR, >BR, >C═O, >S═O, >S(═O)$_2$, >PR, >$SiR_2$, >$GeR_2$, >P(═O)R, and >$BR_2$, said R being hydrogen, halogen, alkyl, aryl, alkoxy, carboxylic acid, ester, amide, an aromatic, heteroaromatic or non-aromatic ring, or may form a fused ring together with Ca or the cyclometallated ring. Preferably. L is a single bond.

The metal complex of the present invention can be used in various applications, including OLED, photovoltaic cells, sensing, labels or organic semiconductor devices. In particular, those compounds can act as efficient phosphorescent and stable emitters for OLEDs.

The present invention also provides a device, preferably a light emitting device, comprising the disclosed metal complex.

DESCRIPTION OF EMBODIMENTS

It is generally accepted that the instability of the FIrpic complex may be attributed to the following reasons: (1) the fluorine-aromatic carbon bond is poorly stable, and (2) the proton between the two fluorine atoms becomes highly acidic due to the strong acceptor character of the two fluorine atoms. As both reasons are directly related to the presence of the fluorine atoms, solutions to replace these substituents by more stable ones while keeping high luminescence and processability, are highly sought after. However, up to now, main research has been conducting towards different skeletons for the main ligand than the phenyl-pyridine used in FIrPic. This approach is expected to fundamentally modify the electrochemical and photophysical properties of the phosphorescent dopant compared to the widely studied and optimized FIrPic.

The present invention is based on the technical concept of replacing the two fluorine atoms with a new substitution pattern using various donor and acceptor groups in order to tune the HOMO and LUMO energy levels of metal complexes to obtain similar energy levels than FIrPic, to easily keep already developed and optimized materials and device architectures to keep the high efficiency of the device, and to improve the stability thereof due primary to the absence of fluorine substituents.

Usually only acceptor groups are attached on the orthometallated phenyl ring in order to obtain blue emission. This is because the acceptor character of the substituents strongly stabilizes the HOMO energy level, more than it stabilizes the LUMO energy level. However, as more and more acceptor groups are attached to the orthometallated phenyl ring, the HOMO and LUMO energy levels are more and more stabilized, which requires the development of new host and charge carrier materials with suitable HOMO and LUMO levels for keeping high device efficiency. Despite such common knowledge, the inventors discovered that when donor groups on the orthometallated phenyl ring are introduced, it can induce a blue shift in the emission color, e.g., by destabilizing the LUMO energy level more than the HOMO energy orbital, leading to an increased HOMO-LUMO gap which translates into a blue shift compared to the hydrogen-substituted ligand. Metal complexes with similar electrochemical and photophysical properties to FIrpic and with better stability, can be obtained by finally attaching a strong acceptor group between the two donor groups.

The present invention provides a metal complex having a partial structure represented by Formula (I-0) or a tautomer thereof:

Formula (I-0)

wherein

Cy is a 5 to 7 membered ring, preferably a 6-membered ring, which may be aromatic, non aromatic or partially aromatic and which coordinates to the metal atom through a carbon atom;

A is a nitrogen atom;

a is an integer equal or superior to 1;

D is an electron donor group; and b is an integer equal or superior to 1.

In some specific embodiments, the ligand of the metal complex of the present invention is represented by the formula (I) below or a tautomer thereof:

Formula (I)

wherein

A is a nitrogen atom, $D^1$ and $D^2$ are electron donor groups, the same or different at each occurrence, preferably any one selected from a group consisting of amino, $C_1$-$C_{20}$ alkoxy, and $C_1$-$C_{20}$ alkyl groups, Ca is a neutral ring capable of coordination to the metal atom, X is independently selected from substituents, with at least one substituent X being hydrogen, n is an integer from 1 to 2, y is an integer from 1 to 2, with the proviso that n+y is not more than 3, L is any one selected from a single bond, —S—, —O—, —Se—, >$CR_2$, >NR, >BR, >C=O, >S=O, >S(=O)$_2$, >PR, >$SiR_2$, >$GeR_2$, >P(=O)R, and >$BR_2$, said R being hydrogen, halogen, alkyl, alkoxy, carboxylic acid, ester, amide, an aromatic, heteroaromatic or non-aromatic ring, or may form a fused ring together with Ca or the cyclometallated ring. Preferably L is a single bond.

In more specific embodiments, Ca comprises a substituted or unsubstituted heterocyclic ring. Such heterocyclic ring includes, but is not limited to, pyridine, imidazole, pyrazole, furan, indole, pyrimidine, pyrrole, etc.

The term "electron donor," as used herein, is an atom or a group of atoms that have a negative Hammett parameter. The electron donors which are used in the present invention include, without being limited to, amino, $C_1$-$C_{20}$ alkoxy, and $C_1$-$C_{20}$ alkyl groups.

In a more specific embodiment, the complexes using the following ligands are included:

In the above formulae, $R^1$ to $R^6$, which may be the same or different, individually refers to any substituent from hydrogen, alkyl, alkoxy, or an aromatic, heteroaromatic or non-aromatic ring, and Y is independently selected from substituents other than hydrogen and p is an integer from 0 to 4, provided that $R^1$ and $R^2$ may not both be hydrogen at the same time.

In other embodiments, the metal complexes optionally comprise an ancillary ligand. The ancillary ligand may be any one known in the art but preferably is a mono- or bidendate ligand. Suitable bidentate ligands include, but are not limited to, acetylacetonate (acac), picolinate (pic), substituted picoli- nate, hexafluoroacetylacetonate, salicylidene, 8-hydroxyquinolinate; amino acids, salicylaldehydes, and iminoacetonates, ethylene diamine derivatives, amidinate, biphenyl, bipyridyl, phenylpyridyl, 2-(1-naphthyl)benzoxazole, 2-phenylbenzoxazole, 2-phenylbenzothiazole, coumarin, thienylpyridine, benzothienylpyridine, thienylpyridine, tolylpyridine, phenylimines, vinylpyridines, arylquinolines, pyridylnaphthalenes, pyridylpyrroles, pyridylimidazoles, phenylindoles, derivatives thereof, and mixtures thereof.

In another embodiment, the ancillary ligand can each be a monodentate ligand, that is, any ligand capable of coordinating to a metal atom through one atom. Numerous monodentate ligands are well known in the art, and suitable examples include halogen, such as chlorine atom (Cl), halogen ions, cyanide, cyanate, isocyanate, thiocyanate, nitrile, isocyanide, pyridine, imidazole, pyrazole, sulfite ion, or thiosulfate.

In another aspect of the present invention, the metal complex can be represented by any of the following formulae:

-continued

The above mentioned iridium complexes can exhibit a phosphorescent emission in the visible region of the spectrum. In specific embodiments, the emissive complex exhibits a phosphorescent emission in the blue region of the spectrum.

Another aspect of the present invention relates to an OLED comprising the metal complex comprising the ligand of Formula (I). Other aspects of the present invention relate to use of the metal complex having the ligand of Formula (I) in an OLED.

The OLED device generally comprises:

a glass substrate;

a generally transparent anode such as an indium-tin oxide (ITO) anode;

a hole transporting layer (HTL);

an emissive layer (EML);

generally a hole and exciton blocking layer;

an electron transporting layer (ETL); and a generally metallic cathode such as an Al layer. The emissive layer usually comprises the emissive material, same including the metal complex of the present invention, and also comprises a host material (where the emissive material is present as a dopant). The host material is known in the art, as described in US 2010/0190984, the disclosures of which is incorporated herein in its entirety.

If the metal complex of the present invention is used as a dopant in a host layer which is known in the art, then it is generally used in an amount of at least 1 wt %, specifically at least 3 wt %, and more specifically at least 5 wt %, with respect to the total weight of the host and the dopant. Further, it is generally used in an amount of at most 30 wt %, specifically at most 25 wt %. In a phosphorescent emitting device, holes from the hole transport layer recombine in the emissive layer with electrons from the electron transport layer to form triplet-based excitons. As the triplet-based excitons diffuse over a relatively long distance in the emissive layer before emitting light, some of the excitons may diffuse to the cathode and are quenched by the cathode, resulting in non-radiative exciton decay. In order to reduce the quenching by the cathode, a hole blocking layer is disposed between the cathode and the emissive layer. The blocking layer can be made of N,N'-diphenyl-N,N'-bis-alpha-anpthylbenzidine (NPD), CBP, aluminum tris (8-hydroxyquioline) ($Alq_3$) and bathocuproine (BCP), for example. Details of such other layers are described in many references, such as US 2010/0190984.

The present invention also relates to a use of the metal complex according to the present invention in photovoltaic cells, sensing devices, labels or organic semiconductor devices.

EXAMPLES

Hereinafter, the present invention will be explained in detail with reference to examples and comparative examples. These examples, however, should not in any sense be interpreted as limiting the scope of the present invention. Further, units are expressed by weight unless otherwise described.

Synthetic Methods

Synthetic Examples

Example 1

Procedure for EB288

Ligand 2',6'-dimethoxy-2,3'-bipyridine [as a 0.2H$_2$O solvate]

2-Bromopyridine (0.475 mL, 0.78 g, 4.9 mmol) and 2,6-dimethoxy-3-pyridineboronic acid (1.09 g, 6.0 mmol, excess) were dissolved in THF (25 mL) at RT. Aqueous solution of K$_2$CO$_3$ (1.65 g in 10 mL of water, 12 mmol, excess) was added, followed by Pd(PPh$_3$)$_4$ (295 mg, 0.25 mmol). The mixture was stirred at 90° C. for 20 h under argon to give yellow solution. Organic solvent was removed under reduced pressure and the residue was extracted with dichloromethane and water. Evaporation of organic phase provided red oil that was purified by chromatography on silica gel eluting with CH$_2$Cl$_2$/MeOH 0 to 0.2%. The fractions containing pure product were collected, while those containing impurities were again purified by chromatography using the same conditions. After three chromatographic purifications the total yield was 965 mg (4.39 mmol; 90%) of yellow oil that crystallized as yellow solid on standing. Anal. Calcd for C$_{12}$H$_{12}$N$_2$O$_2$.0.2H$_2$O (MW 219.84): C, 65.56; H, 5.69; N, 12.74. Found: C, 65.74; H, 5.63; N, 12.53. $^1$H NMR (400 MHz, CD$_2$Cl$_2$): 8.64 (d, J 4.0, 1H), 8.32 (d, J 8.0, 1H), 8.03 (d, J 8.0, 1H), 7.74 (t, J 8.0, 1H), 7.19 (m, 1H), 6.47 (d, J 8.0, 1H), 4.06 (s, 3H), 4.00 (s, 3H). $^{13}$C NMR (100 MHz, CD$_2$Cl$_2$): 163.24, 160.16, 154.36, 149.44, 142.44, 136.01, 123.97, 121.38, 114.30, 102.02, 53.75, 53.52.

Precursor Complex [Ir(C^N)$_2$Cl]$_2$

Reaction was performed under argon with solvents that were de-oxygenated (by bubbling with Ar) but not dried. IrCl$_3$.3H$_2$O (281 mg, 0.80 mmol) was completely dissolved in 2-ethoxyethanol (25 mL) to give purple solution. Water (7.5 mL) was added; the solution was warmed to 60° C. followed by addition of the ligand 2',6'-dimethoxy-2,3'-bipyridine (used as a 0.2H$_2$O solvate; 431 mg, 1.96 mmol, excess). The solution immediately changed colour to brown. It was stirred at 80° C. overnight to give a dark red solution and grey precipitate. Reaction mixture was cooled to RT and filtered. The solid was thoroughly washed with water and ether. Grey solid: 33 mg (0.025 mmol; 6%; C$_{48}$H$_{44}$Cl$_2$Ir$_2$N$_8$O$_8$; MW 1316.25); soluble in CH$_2$Cl$_2$; insoluble in methanol. $^1$H NMR (400 MHz, CD$_2$Cl$_2$): 9.07 (dd, J 5.6, J 0.8, 4H), 8.57 (d, J 7.6, 4H), 7.83-7.73 (m, 4H), 6.76-6.67 (m, 4H), 4.79 (s, 4H), 4.03 (s, 12H), 3.66 (s, 12H).

EB288

EB288

To a solution of the precursor dimer complex (22 mg, 0.0167 mmol) in dichloromethane (DCM, 30 mL) was added picolinic acid (14 mg, 0.11 mmol) and tetrabutyl ammonium hydroxide (TBAOH, 48 mg, 0.06 mmol). The mixture was heated at 35° C. overnight under argon. The volume of the solution obtained was reduced under reduced pressure to about ⅓ and passed through a silica gel plug eluting with dichloromethane/methanol. The yellow band was collected, evaporated to dryness, dissolved in the minimum of dichloromethane and precipitated with hexane. The solid was filtered, washed with hexane and dried. EB288 was obtained as a pale yellow solid (21 mg, 84%)

$^1$H NMR (CDCl$_3$, 400 MHz): d 8.68 (dd, 1H); 8.54 (dd, 1H); 8.45 (dd, 1H); 8.32 (dd, 1H); 7.92 (dt, 1H); 7.88 (dd, 1H); 7.67 (ddd, 2H); 7.38 (dd, 1H); 7.36 (dd, 1H); 7.02 (dt, 1H); 6.80 (dt, 1H); 5.44 (s, 1H); 5.20 (s, 1H); 4.09 (s, 3H); 4.03 (s, 3H); 3.82 (s, 3H); 3.75 (s, 3H).

Example 2

Procedure for EB318

2,6-bis(2,2,6,6-tetramethylpiperidin-1-yl)pyridine

To a 1,4-dioxane solution (30 ml) of 2,2,6,6-tetramethylpiperidine (3.11 g, 22.0 mmol) and potassium-bis(trimethylsilyl)amide (4.39 g, 22.0 mmol)₂ was added 2,6-dibromopyridine (2.37 g, 10.0 mmol). The reaction mixture was stirred vigorously at 100° C. overnight. After cooling down to room temperature, the reaction was quenched with water and extracted with diethyl ether/THF (1:1) mixtures. The combined extracts were washed with 1 M Na₂CO₃, dried over MgSO₄, filtrated, and evaporated to dryness. The product was purified by flash chromatography on silica gel leading to colorless oil ($R_f$=0.5 in Ethylacetate:hexane=1:20, Yield=1.13 g (31.6%))

¹H NMR (400 MHz, CDCl₃): 7.39 (t, J=7.6 Hz, 1H), 6.79 (d, J=8.0 Hz, 2H), 1.74 (m, 4H), 1.52 (t, J=6 Hz, 8H), 1.13 (s, 24H). ¹³C NMR (100 MHz, CDCl₃): 159.24, 135.95, 126.20, 54.29, 41.94, 29.72, 18.50.

3-Bromo-2,6-bis(2,2,6,6-tetramethylpiperidin-1-yl) pyridine

Reaction was performed under air. To a ice-cooled solution of 2,6-bis(2,2,6,6-tetramethylpiperidin-1-yl)pyridine (1 g, 2.8 mmol) in acetonitrile (100 ml) was added NBS (0.45 g, 2.5 mmol) portion-wise over 30 min. The reaction mixture was stirred at –0° C. for 2 h, until the color of the solution disappeared and then stirred overnight at room temperature. The reaction was quenched with water (100 mL) and the product extracted by ethylacetate. The product was purified by column chromatography on silica gel and obtained as white solid ($R_f$=0.6 in Ethylacetate:hexane=1:20, Yield=0.53 g (43.4%))

¹H NMR (400 MHz, CDCl₃): 7.76 (d, J=8.0 Hz, 1H), 6.72 (d, J=8.0 Hz, 1H), 1.98-1.50 (m, 12H), 1.45 (s, 6H), 1.16 (s, 12H), 0.93 (s, 6H). ¹³C NMR (100 MHz, CDCl₃): 158.76, 156.91, 141.20, 127.86, 124.53, 55.67, 54.44, 41.73, 40.97, 31.20, 25.48, 18.72, 18.39.

2',6'-bis(2,2,6,6-tetramethylpiperidin-1-yl)-2,3'-bipyridine

A mixture of 3-Bromo-2,6-bis(2,2,6,6-tetramethylpiperidin-1-yl)pyridine (0.4 g, 0.92 mmol), 2-(tributylstannyl)pyridine (0.4 g, 1.10 mmol), Pd(PPh₃)₄ (0.053 g, 0.046 mmol), and Cesium fluoride (0.28 g, 1.83 mmol) in Toluene (30 ml) was stirred under reflux for 2 days. After cooling down to room temperature the reaction was quenched with saturated CsF aqueous solution (100 mL). The product was extracted with ethylacetate. The product was purified by column chromatography on silica gel and obtained as white solide ($R_f$=0.5 in Ethylacetate:hexane=1:4, Yield=50 mg (12.5%))

¹H NMR (400 MHz, CDCl₃): 8.68-8.64 (m, 2H), 8.24 (d, J=8.0 Hz, 1H), 7.67 (td, J=8.0, 2.0 Hz, 1H), 7.16 (dd, J=6.8, 4.8 Hz, 1H), 6.97 (d, J=8.0 Hz, 1H), 2.00-1.52 (m, 12H), 1.47 (s, 6H), 1.18 (s, 12H), 0.77 (s, 6H). ¹³C NMR (100 MHz, CDCl₃): 159.52, 158.15, 156.81, 149.28, 139.37, 135.07, 133.35, 127.18, 124.84, 121.55, 56.03, 54.36, 41.87, 40.43, 31.61, 26.35, 18.69, 18.44.

Example 3

Procedure for EB317

EB317

As other dimer, with reaction temperature 95° C. Obtained as a yellow solid.

Example 4

Procedure for EB318

EB318

EB318 was obtained in a similar manner to EB288 using 4-dimethylamino-picolinic acid instead of picolinic acid.

Example 5

Procedure for EB321

EB321

[Ir(COD)Cl]$_2$ dimer (2.098 g, 3.12 mmol) was suspended in 10 mL of 2-ethoxyethanol in a 50 mL flask. The suspension was filled with argon by 3 cycles vacuum/argon. The C^N ligand (2.52 g, 12.58 mmol) was added and 1 mL of 2-ethoxyethanol was used for rinsing. The suspension turned to a yellow solution almost immediately and it was filled again with argon by 3 cycles vacuum/argon. The flask was closed and heated at 125° C. for 4 hours. Upon heating the solution darkened to a deep red-orange color. Within half an hour a yellow precipitate appeared. After 4 hours, the suspension was cooled to room temperature and 30 mL of methanol was added and the precipitate filtered, washed with methanol and dried. EB321 was obtained as a pale yellow solid (2.48 g, 1.98 mmol, yield=64%)

When $^1$H-NMR was taken in pure CDCl$_3$, two major signal patterns (100% and 40%) were observed in addition of at least two patterns (<10% intensity)

$^1$H NMR (CDCl$_3$, 400 MHz), main pattern 100%: δ 9.91 (dd, 1H, J=5.6, 0.8 Hz); 8.04 (d, 1H, J=8.4 Hz); 7.90 (dt, 1H, J=8.4, 1.6 Hz); 7.39 (dt, 1H, J=6.0, 1.2 Hz); 5.33 (s, 1H); 3.74 (s, 3H); 2.77 (s, 3H).

$^1$H NMR (CDCl$_3$, 400 MHz), second pattern 40%: δ 9.21 (dd, 1H, J=5.6, 0.8 Hz); 8.04 (d, 1H, J=8.4 Hz); 7.80 (dt, 1H, J=8.4, 1.6 Hz); 6.78 (dt, 1H, J=6.0, 1.2 Hz); 5.04 (s, 1H); 3.66 (s, 3H); 2.79 (s, 3H).

When few drops of DMSO-d6 (deuterated dimethyl sulfoxide) were added, the spectrum turned very clean, as only one pattern was observed, and showed the expected dissymmetric pattern for a mono-chloro/mono-dmso bis-cyclometalated complex:

$^1$H NMR (CDCl$_3$, 400 MHz): δ 9.89 (d, 1H, J=5.2 Hz); 9.84 (d, 1H, J=5.2 Hz); 8.04 (d, 1H, J=8.4 Hz); 8.01 (d, 1H, J=8.4 Hz); 7.92 (t, 1H, J=8.0 Hz); 7.82 (t, 1H, J=8.0 Hz); 7.29 (t, 1H, J=6.0 Hz); 7.23 (t, 1H, J=6.0 Hz); 5.66 (s, 1H); 4.94 (s, 1H); 3.74 (s, 3H); 3.68 (s, 3H); 2.76 (s, 3H); 2.73 (s, 3H).

Example 6

Procedure for EB343

EB343

EB343: Picolinic acid (0.413 g, 3.35 mmol) in DCM (5 mL) was added to TBAOH (2.8 g, 3.50 mmol) in methanol (5 mL). Once everything was dissolved and a clear solution was obtained, it was added by portion to a suspension of EB321 (1.50 g, 1.20 mmol) in dichloromethane (150 mL). The mixture was refluxed (45° C.) overnight. The volatiles were evaporated and the crude dissolved in methanol and water was added. After 2 hours in the refrigerator, the precipitate was filtered and washed with water and cold methanol and dried. EB343 was obtained as a bright yellow solid (1.105 g, 1.55 mmol, yield=65%)

$^1$H NMR (CDCl$_3$, 400 MHz): δ 8.82 (dd, 1H, J=6.0, 1.2 Hz); 8.34 (dd, 1H, J=8.0, 0.8 Hz); 8.06 (d, 1H, J=8.4 Hz); 8.02 (d, 1H, J=8.4 Hz); 7.94 (dt, 1H, J=8.0, 1.2 Hz); 7.77 (m, 3H); 7.50 (dd, 1H, J=6.0, 1.2 Hz); 7.39 (ddd, 1H, J=7.6, 5.6, 1.6

Hz); 7.13 (ddd, 1H, J=8.8, 6.0, 1.6 Hz); 6.90 (ddd, 1H, J=8.8, 6.0, 1.6 Hz); 5.64 (s, 1H); 5.35 (s, 1H); 3.83 (s, 3H); 3.76 (s, 3H); 2.84 (s, 3H); 2.79 (s, 3H).

$^{13}$C NMR (CDCl$_3$, 100 MHz): δ 172.81, 167.62, 166.05, 163.58, 162.95, 161.96, 161.57, 153.41, 153.13, 151.85, 149.48, 148.72, 148.17, 138.32, 137.58, 137.54, 135.17, 134.95, 128.64, 128.44, 122.65, 122.12, 121.64, 121.39, 111.04, 110.93, 53.16, 53.09, 26.61, 26.46.

HR-MS (ES): m/z=714.1712 [M+H]$^+$ (calc. 714.1694).

Example 7

Procedure for EB370

EB370

EB370: Acetylacetone (0.267 g, 2.67 mmol) in DCM (5 mL) was added to TBAOH (1.9 g, 2.37 mmol) in methanol (5 mL). Once everything was dissolved and a clear yellowish solution was obtained, it was added by portion to a suspension of EB321 (0.833 g, 0.66 mmol) in dichloromethane (80 mL). The mixture was refluxed (45° C.) overnight. The volatiles were evaporated and the crude suspended in methanol. After 2 hours in the refrigerator, the precipitate was filtered and washed with cold methanol and dried. This intermediate crude was further purified by silica gel chromatography column using DCM/ethylacetate/MeOH (100/15/2; v/v/v) as eluent. The fraction containing the product was evaporated to dryness, dissolved in the minimum amount of DCM and hexane was added (~3 times the volume of DCM). The DCM was slowly evaporated under vacuum and the remaining suspension kept in the refrigerator overnight. It was then filtered, washed with hexane and dried to afford EB370 as a bright yellow solid (0.812 g, 1.18 mmol, yield=88%)

$^1$H NMR (CDCl$_3$, 400 MHz): δ 8.52 (ddd, 2H, J=5.7, 1.7, 0.7 Hz); 8.02 (dd, 2H, J=8.4, 0.5 Hz); 7.79 (ddd, 2H, J=8.4, 7.4, 1.7 Hz); 7.13 (ddd, 2H, J=7.3, 5.8, 1.4 Hz); 5.47 (s, 2H); 5.24 (s, 1H); 3.75 (s, 6H); 2.78 (s, 6H); 1.81 (s, 6H).

Example 8

Procedure for EB323

EB323

[Ir(COD)Cl]$_2$ dimer (2.00 g, 2.98 mmol) was suspended in 9 mL of 2-ethoxyethanol in a 50 mL flask. The suspension was filled with argon by 3 cycles vacuum/argon. The C^N ligand (2.56 g, 11.95 mmol) was added and 1 mL of 2-ethoxyethanol was used for rinsing. The suspension turned to a yellow solution almost immediately and it was filled again with argon by 3 cycles vacuum/argon. The flask was closed and heated at 125° C. for 4 hours. Upon heating the solution darkens to a deep red-orange color. Within half an hour a yellow precipitate appears. After 4 hours, the suspension was cooled to room temperature and 30 mL of methanol was added and the precipitate filtered, washed with methanol and dried. EB323 was obtained as a pale yellow solid (3.084 g, 2.36 mmol, yield=79%)

$^1$H NMR (CDCl$_3$, 400 MHz): δ 9.02 (d, 4H, J=6.0 Hz); 7.84 (bs, 4H); 6.55 (dd, 4H, J=6.0, 1.6 Hz); 5.09 (s, 4H); 3.67 (s, 12H); 2.78 (s, 12H); 2.66 (s, 12H).

Example 9

Procedure for EB332

EB332

EB332: Acetylacetone (0.445 g, 4.44 mmol) in DCM (5 mL) was added to TBAOH (3.19 g, 3.99 mmol) in methanol (5 mL). Once everything was dissolved and a clear yellowish solution was obtained, it was added by portion to a suspension of EB323 (1.45 g, 1.11 mmol) in dichloromethane (150 mL). The mixture was refluxed (45° C.) overnight. The volatiles were evaporated and the crude suspended in methanol. After 2 hours in the refrigerator, the precipitate was filtered and washed with cold methanol and dried. This intermediate crude was further purified by silica gel chromatography column using DCM/ethylacetate/MeOH (100/15/2; v/v/v) as eluent. The fraction containing the product was evaporated to dryness, dissolved in the minimum amount of DCM and hexane was added (~3 times the volume of DCM). The DCM was slowly evaporated under vacuum and the remaining suspension kept in the refrigerator overnight. It was then filtered, washed with hexane and dried to afford EB332 as a bright yellow solid (1.355 g, 1.89 mmol, yield=85%)

$^1$H NMR (CDCl$_3$, 400 MHz): δ 8.34 (d, 2H, J=6.0 Hz); 7.82 (bs, 2H); 6.96 (dd, 2H, J=6.0, 1.2 Hz); 5.49 (s, 2H); 5.22 (s, 1H); 3.75 (s, 6H); 2.78 (s, 6H); 2.59 (s, 6H); 1.79 (s, 6H).

$^{13}$C NMR (CDCl3, 100 MHz): δ 184.88, 166.44, 162.89, 160.91, 152.02, 148.52, 148.05, 135.93, 122.92, 121.88, 111.82, 100.64, 52.87, 28.98, 26.49, 22.02.

HR-MS (ES): m/z=719.2202 [M+H]$^+$ (calc. 719.2211).

Anal: Calcd. for C$_{31}$H$_{33}$IrN$_4$O$_4$: C, 51.87; H, 4.63; N, 7.80. Found C, 51.07; H, 4.63; N, 7.70.

Example 10

Procedure for EB346

EB346

[Ir(COD)Cl]$_2$ dimer (0.526 g, 0.78 mmol) was suspended in 4 mL of 2-ethoxyethanol in a 25 mL flask. The suspension was filled with argon by 3 cycles vacuum/argon. The C^N ligand (0.803 g, 3.13 mmol) was added and 1 mL of 2-ethoxyethanol was used for rinsing. The reddish suspension turned colorless almost immediately and it was filled again with argon by 3 cycles vacuum/argon. The flask was closed and heated at 125° C. for 4 hours. Upon heating the solution darkened to a deep red-orange color. Within half an hour a yellow precipitate appeared. After 4 hours, the suspension was cooled to room temperature and 30 mL of methanol was added and the precipitate filtered, washed with methanol and dried. EB346 was obtained as a pale yellow solid (1.149 g, 0.78 mmol, yield=99%)

$^1$H NMR (CDCl$_3$, 400 MHz): δ 9.02 (d, 4H, J=5.6 Hz); 8.44 (s, 4H); 6.54 (dd, 4H, J=6.0, 1.2 Hz); 5.55 (s, 4H); 4.00 (s, 12H); 2.65 (s, 12H); 0.97 (s, 36H).

Example 11

Procedure for EB349

EB349

EB349: Acetylacetone (0.224 g, 2.24 mmol) in DCM (5 mL) was added to TBAOH (1.8 g, 2.25 mmol) in methanol (5 mL). Once everything was dissolved and a clear yellowish solution was obtained, it was added by portion to a suspension of EB346 (1.1 g, 0.75 mmol) in dichloromethane (100 mL). The mixture was refluxed (45° C.) overnight. The volatiles were evaporated and the crude suspended in methanol. After 2 hours in the refrigerator, the precipitate was filtered and washed with cold methanol and dried. EB349 was obtained as a bright yellow solid (1.028 g, 1.28 mmol, yield=86%)

$^1$H NMR (CDCl$_3$, 400 MHz): δ 8.38 (d, 2H, J=0.8 Hz); 8.30 (d, 2H, J=5.6 Hz); 6.94 (ddd, 2H, J=6.0, 2.0, 0.4 Hz); 5.81 (s, 2H); 5.20 (s, 1H); 4.02 (s, 6H); 2.61 (s, 6H); 1.80 (s, 6H); 1.09 (s, 18H).

$^{13}$C NMR (CDCl$_3$, 100 MHz): δ 184.65, 166.41, 164.09, 164.01, 158.78, 148.62, 147.46, 125.87, 123.46, 121.31, 117.78, 100.55, 52.49, 36.72, 30.07, 28.95, 21.83.

HR-MS (ES): m/z=803.3158 [M+H]$^+$ (calc. 803.3151).

Anal: Calcd. for C$_{37}$H$_{45}$IrN$_4$O$_4$: C, 55.41; H, 5.66; N, 6.99. Found C, 55.17; H, 5.75; N, 7.14.

Example 12

Procedure for EB348

EB348

[Ir(COD)Cl]$_2$ dimer (1.30 g, 1.93 mmol) was suspended in 10 mL of 2-ethoxyethanol in a 50 mL flask. The suspension was filled with argon by 3 cycles vacuum/argon. The C^N ligand (2.08 g, 7.75 mmol) was added and 5 mL of 2-ethoxyethanol was used for rinsing. The reddish suspension turned colorless almost immediately and it was filled again with argon by 3 cycles vacuum/argon. The flask was closed and heated at 125° C. for 4 hours. Upon heating the solution darkened to a deep red-orange color. Within half an hour a yellow precipitate appeared. After 4 hours, the suspension was cooled to room temperature and 30 mL of methanol was added and the precipitate filtered, washed with cold methanol and dried. EB348 was obtained as a yellow solid (1.64 g, 1.076 mmol, yield=56%)

$^1$H NMR (CDCl$_3$, 400 MHz): δ 9.61 (s, 4H); 8.17 (d, 4H, J=9.2 Hz); 7.99 (dd, 4H, J=8.8, 2.0 Hz); 4.83 (s, 4H); 3.68 (s, 12H); 2.82 (s, 12H).

Example 13

Procedure for EB351

EB351

EB351: Picolinic acid (0.260 g, 2.11 mmol) in DCM (5 mL) was added to TBAOH (1.65 g, 2.06 mmol) in methanol (5 mL). Once everything was dissolved and a clear solution was obtained, it was added by portion to a suspension of EB348 (1.20 g, 0.79 mmol) in dichloromethane (100 mL). The mixture was refluxed (45° C.) overnight. The volatiles were evaporated and the crude dissolved in methanol and water (about 1/10 of the volume) was added. Upon sonication a large yellow precipitate formed. After 2 hours in the refrigerator, the precipitate was filtered and washed with water and briefly with cold methanol and dried. EB351 was obtained as a bright yellow solid (1.152 g, 1.36 mmol, yield=86%)

$^1$H NMR (CDCl$_3$, 400 MHz): δ 9.06 (s, 1H); 8.39 (d, 1H, J=7.6 Hz); 8.17 (m, 2H); 8.05-7.94 (m, 3H); 7.79 (d, 1H, J=4.8 Hz); 7.54 (s, 1H); 7.48 (ddd, 1H, J=7.6, 5.6, 1.6 Hz); 5.60 (s, 1H); 5.31 (s, 1H); 3.86 (s, 3H); 3.80 (s, 3H); 2.89 (s, 3H); 2.81 (s, 3H).

HR-MS (ES): m/z=850.1439 [M+H]$^+$ (calc. 850.1442).

Anal: Calcd. for C$_{32}$H$_{24}$F$_6$IrN$_5$O$_4$: C, 45.28; H, 2.85; N, 8.25. Found C, 45.07; H, 2.43; N, 8.27.

Example 14

Procedure for EB344

EB344

[Ir(COD)Cl]$_2$ dimer (1.097 g, 1.63 mmol) was suspended in 9 mL of 2-ethoxyethanol in a 50 mL flask. The suspension was filled with argon by 3 cycles vacuum/argon. The C^N ligand (1.505 g, 6.54 mmol) was added and 1 mL of 2-ethoxyethanol was used for rinsing. The reddish suspension turned colorless almost immediately and it was filled again with argon by 3 cycles vacuum/argon. The flask was closed and heated at 125° C. for 3 hours. Upon heating the solution darkened to a deep orange color. Within half an hour a yellow precipitate appeared. After 3 hours, the suspension was cooled to room temperature and 30 mL of methanol was added and the precipitate filtered, washed with cold methanol and dried. EB344 was obtained as a pale yellow solid (2.00 g, 1.46 mmol, yield=89%)

$^1$H NMR (CDCl$_3$, 400 MHz): δ 8.89 (d, 4H, J=6.0 Hz); 8.32 (s, 4H); 6.45 (dd, 4H, J=5.6, 1.6 Hz); 4.94 (s, 4H); 4.01 (s, 12H); 3.64 (s, 12H); 2.62 (s, 12H).

Example 15

Procedure for EB353

EB353

EB353: 3-methyl-picolinic acid (0.464 g, 3.38 mmol) in DCM (5 mL) was added to TBAOH (2.40 g, 3.00 mmol) in methanol (5 mL). Once everything was dissolved and a clear solution was obtained, it was added by portion to a suspension of EB344 (1.402 g, 1.094 mmol) in dichloromethane (150 mL). The mixture was refluxed (45° C.) overnight. The volatiles were evaporated and the crude suspended in methanol. After 2 hours in the refrigerator, the precipitate was filtered and washed with methanol and dried. EB351 was obtained as a pale yellow solid (1.568 g, 1.99 mmol, yield=91%)

$^1$H NMR (CDCl$_3$, 400 MHz): δ 8.52 (d, 1H, J=6.0 Hz); 8.32 (d, 1H, J=0.8 Hz); 8.24 (d, 1H, J=0.8 Hz); 7.74 (d, 1H, 5.2 Hz); 7.65 (d, 1H, J=7.6 Hz); 7.18 (m, 2H); 6.86 (dd, 1H, J=6.0, 1.6 Hz); 6.63 (dd, 1H, J=6.0, 1.6 Hz); 5.43 (s, 1H); 5.21 (s, 1H); 4.08 (s, 3H); 4.02 (s, 3H); 3.80 (s, 3H); 3.74 (s, 3H); 2.86 (s, 3H); 2.50 (s, 6H).

$^{13}$C NMR (CDCl$_3$, 100 MHz): δ 173.36, 167.13, 166.94, 166.08, 164.67, 162.11, 161.65, 159.76, 159.61, 148.97, 148.92, 148.77, 147.78, 147.08, 146.89, 141.76, 141.08, 127.27, 123.61, 123.01, 121.84, 121.70, 121.04, 120.74, 105.71, 105.63, 53.23, 53.22, 53.16, 53.14, 21.82, 21.75, 20.88.

HR-MS (ES): m/z=788.2040 [M+H]$^+$ (calc. 788.2062).

Example 16

Procedure for EB356

EB356

[Ir(COD)Cl]$_2$ dimer (0.83 g, 1.23 mmol) was suspended in 8 mL of 2-ethoxyethanol in a 50 mL flask. The suspension was filled with argon by 3 cycles vacuum/argon. The C^N ligand (1.54 g, 4.96 mmol) was added and 3 mL of 2-ethoxyethanol was used for rinsing. The reddish suspension turned colorless almost immediately and it was filled again with argon by 3 cycles vacuum/argon. The flask was closed and heated at 125° C. for 4 hours. Upon heating the solution darkened to a deep red-orange color. Within half an hour a yellow precipitate appeared. After 4 hours, the suspension was cooled to room temperature and 30 mL of methanol was added and the precipitate filtered, washed with cold methanol and dried. EB356 was obtained as an orange-yellow solid (1.811 g, 1.07 mmol, yield=86%)

$^1$H NMR (CDCl$_3$, 400 MHz): δ 9.24 (d, 4H, J=6.1 Hz); 8.89 (d, 4H, J=1.8 Hz); 6.88 (dd, 4H, J=6.1, 2.0 Hz); 5.46 (s, 4H); 4.04 (s, 12H); 0.97 (s, 36H).

Example 17

Procedure for EB367

EB367

[Ir(COD)Cl]$_2$ dimer (1.8 g, 2.67 mmol) was suspended in 10 mL of 2-ethoxyethanol in a 50 mL flask. The suspension was filled with argon by 3 cycles vacuum/argon. The C^N ligand (2.32 g, 10.7 mmol) was added and 5 mL of 2-ethoxyethanol was used for rinsing. The reddish suspension turned colorless almost immediately and it was filled again with argon by 3 cycles vacuum/argon. The flask was closed and heated at 125° C. for 4 hours. Upon heating the solution darkens to a deep red-orange color. Within half an hour a yellow precipitate appears. After 4 hours, the suspension was cooled to room temperature and 30 mL of methanol was added and the precipitate filtered, washed with cold methanol and dried. EB367 was obtained as a yellow solid (3.41 g, 2.59 mmol, yield=96%)

$^1$H NMR (CD$_2$Cl$_2$, 400 MHz): δ 9.07 (dd, 4H, J=5.6, 0.8 Hz), 8.57 (d, 4H, J=7.6 Hz), 7.83-7.73 (m, 4H), 6.76-6.67 (m, 4H), 4.79 (s, 4H), 4.03 (s, 12H), 3.66 (s, 12H).

Example 18

Procedure for mer-EB410 mer-EB410

[Ir(COD)(μ-OMe)]$_2$ dimer (501 mg, 0.75 mmol) was suspended in 5 mL of 2-ethoxyethanol in a 50 mL flask. The suspension was filled with argon by 3 cycles vacuum/argon. The C^N ligand (1.74 g, 7.57 mmol, 10 eq.) was added and 3 mL of 2-ethoxyethanol was used for rinsing. A dark precipitate formed immediately. The flask was closed and heated at 140° C. for 70 hours. Upon heating the solution clarified. The suspension was cooled to room temperature and 30 mL of methanol was added and the precipitate filtered, washed with cold methanol and dried. The compound was further purified by silica gel column chromatography using CH$_2$Cl$_2$/MeOH as eluent. Mer-EB410 was obtained as a yellow solid (884 mg, 1.06 mmol, yield=71%)

¹H NMR (CDCl₃, 400 MHz): δ 8.39 (dd, 1H, J=1.3, 0.7 Hz), 8.25 (dd, 1H, J=1.3, 0.7 Hz), 8.21 (dd, 1H, J=1.3, 0.7 Hz), 7.84 (d, 1H, J=5.9 Hz), 7.74 (d, 1H, J=5.9 Hz), 7.26 (d, 1H, J=5.9 Hz), 6.59 (m, 1H), 6.43 (m, 2H), 6.06 (s, 1H), 5.57 (s, 1H), 5.39 (s, 1H), 4.04 (s, 3H), 4.03 (s, 3H), 4.02 (s, 3H), 3.78 (s, 6H), 3.73 (s, 3H), 2.39 (s, 3H), 2.37 (s, 3H), 2.36 (s, 3H).

Example 19

Procedure for fac-EB410 fac-EB410 mer-EB410 (50 mg, 0.06 mmol) was suspended in 10 mL of DMSO in a 250 mL flask. The suspension was filled with argon by 3 cycles vacuum/argon and illuminated with a UV hand-lamp for 6 hours. Water was added and the suspension filtered and washed with water. The compound was further purified by silica gel column chromatography using CH₂Cl₂/MeOH as eluent. Fac-EB410 was obtained as a yellow solid (42 mg, 0.051 mmol, yield=84%)

¹H NMR (CDCl₃, 400 MHz): δ 8.35 (dd, 3H, J=1.8, 0.6 Hz), 7.23 (d, 3H, J=5.6 Hz), 6.59 (ddd, 3H, J=5.7, 1.4, 0.6 Hz), 5.99 (s, 3H), 4.05 (s, 9H), 3.76 (s, 9H), 2.40 (s, 9H).

Electrochemical Analysis from Cyclovoltammetric Measurements

TABLE 1

Comparison HOMO and LUMO of complexes

| | Eox/Fc | λonset | E₀₋₀ | HOMO* | LUMO** |
|---|---|---|---|---|---|
| FIrPic | 0.92 | 445 | 2.78652 | −5.89 | −3.10 |
| EB288 | 1.1 | 445 | 2.78652 | −6.14 | −3.35 |

*HOMO = −1.4 * Eox −4.6

**LUMO = HOMO + E₀₋₀

Photoluminescence Measurement

Figure 1:
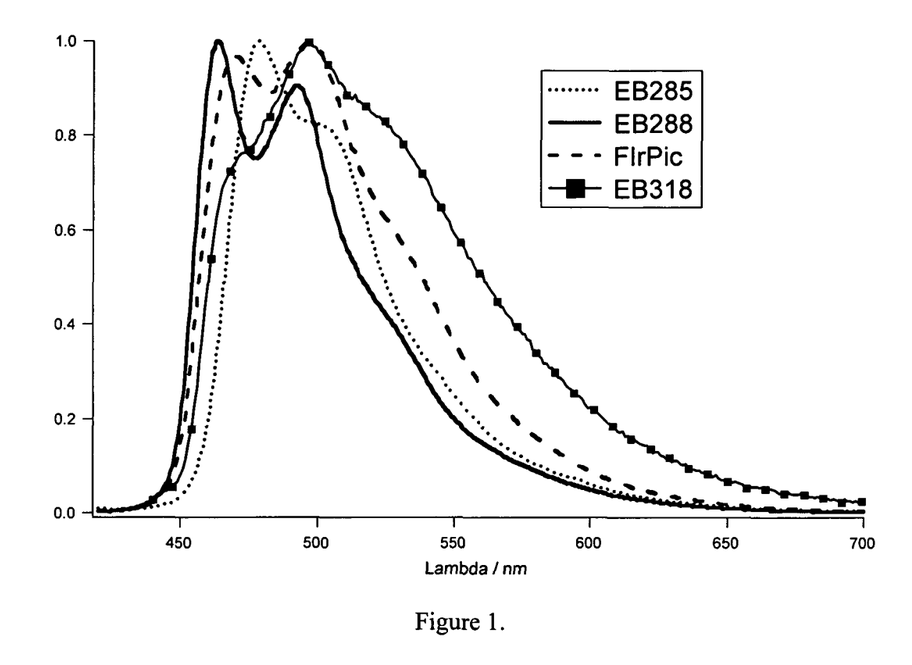
FIG. 1 shows photoluminescent spectra of the present metal complexes in $CH_2Cl_2$, when excited at λexc=400 nm.
Figure 2:
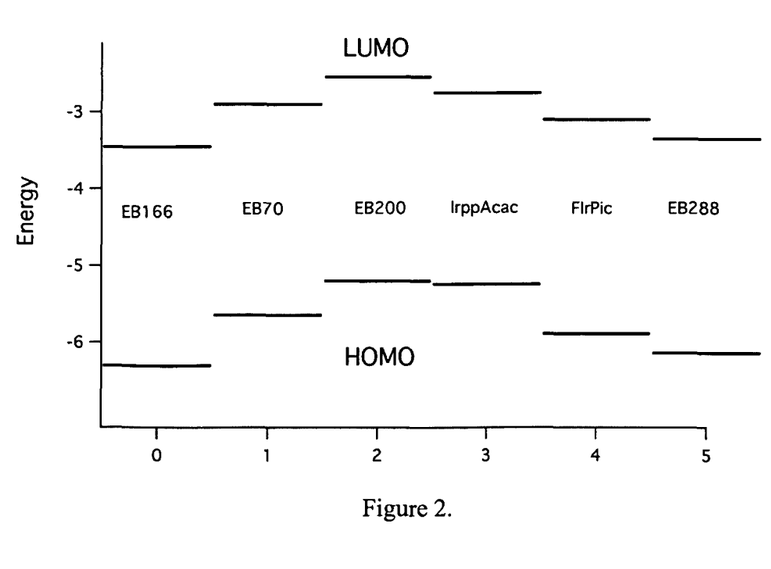
FIG. 2 shows a schematic diagram of HOMO and LUMO energy levels of the metal complexes in Examples and Comparative Examples.

As indicated by FIG. 1, a slight blue shift in the photoluminescence spectra was observed for the metal complexes of the present invention, compared to FIrPic, in view of their emission maxima. Further, as shown in Table 2, the complexes of the invention demonstrated comparable CIE coordinates to FIrPic.

TABLE 2

CIE coordinates of metal complexes of Examples and Comparative Examples

| | x coordinate | y coordinate |
|---|---|---|
| EB288 | 0.161642 | 0.304479 |
| FIrPic (comparative example) | 0.184483 | 0.37841 |

The invention claimed is:

1. A metal complex comprising an Ir atom, an ancillary ligand, wherein the ancillary ligand is picolinate or substituted picolinate, and at least one ligand which coordinates to the Ir atom through a carbon atom, the ligand which coordinates to the Ir atom through a carbon atom represented by any of the following formulae:

wherein R¹ to R⁶, independently from another may be the same or different and are selected from the group consisting of alkyl, alkoxy, and non-aromatic rings, Y is a substituent other than hydrogen and p is an integer from 0 to 4.

2. The metal complex of claim 1 represented by any of the following formulae:

3. A light emitting diode comprising the metal complex according to claim 1.

* * * * *